(12) United States Patent
Chang et al.

(10) Patent No.: US 7,402,411 B2
(45) Date of Patent: Jul. 22, 2008

(54) SPECIES-SPECIFIC PROBES FOR IDENTIFICATION OF TARGET VIRUS AND IDENTIFICATION METHOD USING SAID PROBES

(75) Inventors: Ya-Chun Chang, Taipei (TW); Yueh-Chwen Hsu, Taipei (TW); Tzu-Jung Yeh, Taipei (TW)

(73) Assignee: Bureau of Animal and Plant Health Inspection and Quarantine, Taipei (TW)

( * ) Notice: Subject to any disclaimer, the term of this patent is extended or adjusted under 35 U.S.C. 154(b) by 0 days.

(21) Appl. No.: 11/318,907

(22) Filed: Dec. 27, 2005

(65) Prior Publication Data

US 2007/0148637 A1    Jun. 28, 2007

(51) Int. Cl.
   *C12P 19/34*   (2006.01)
   *C12Q 1/68*    (2006.01)
   *C07H 21/04*   (2006.01)

(52) U.S. Cl. .................. 435/91.2; 435/6; 435/91.5; 536/24.32; 536/24.33

(58) Field of Classification Search .................. None
See application file for complete search history.

(56) References Cited

U.S. PATENT DOCUMENTS

2003/0134293 A1* 7/2003 Liu .............................. 435/6

OTHER PUBLICATIONS

Langeveld et al. Identification of potyviruses using the polymerase chain reaction with degenerate primers. Journal of General Virology (1991) 72: 1531-1541.*
Boonham et al. Detection of potato viruses using microarray technology: towards a generic method for plant viral disease diagnosis. Journal of Virological Methods (2003) 108: 181-187.*
Kong et al. Molecular cloning and nucleotide sequence of coat protein gene of turnip mosaic virus. Nucleic Acids Research (1990) 18(18): 5555.*
Dinant et al. Nucleotide sequence of the 3' terminal region of lettuce mosaic virus potyvirus RNA shows a Gln/Val dipeptide at the cleavage site between the polymerase and the coat protein. Archives of Virology (1991) 116: 235-252.*
Lee et al. Plant virus cDNA chip hybridization for detection and differentiation of four cucurbit-infecting tobamoviruses. Journal of Virological Methods (2003) 110: 19-24.*
Aleman-Verdaguer et al. Analysis of the sequence diversity of the P1, HC, P3, Nlb, and CP genomic regions of several yam mosaic potyvirus isolates: implications for the intraspecies molecular diversity of potyviruses. Journal of General Virology (1997) 78: 1253-1264.*
Buck et al. Design strategies and performance of custom DNA sequencing primers. Biotechniques (1999) 27(3): 528-536.*
GenBank Accession No. AY134473, Jan. 2005, 2 printed pages. Accessed Jun. 9, 2007.*
GenBank Accession No. AB189009. Dec. 2004, 2 printed pages. Accessed Jun. 9, 2007.*
Chen et al. A universal primer to detect members of the Potyviridae and its use to examine the taxonomic status of several members of the family. Archives of Virology (2001) 146: 757-766.*
Timothy M. Rose et al., "Consensus-degenerate hybrid oligonucleotide primers for amplification of distantly related sequences," Nucleic Acids Research, 26(7):1628-1635 (1998).
Penelope A. Bryant et al., "Chips with everything: DNA microarrays in infectious diseases," The Lancet, Infectious Diseases, 4:100-111 (Feb. 2004).
Yueh-Chwen Hsu et al., "A new combination of RT-PCR and reverse dot blot hybridization for rapid detection and identification of potyviruses," Journal of Virological Methods, 128:54-60 (2005).

* cited by examiner

Primary Examiner—Kenneth R. Horlick
Assistant Examiner—Angela Bertagna
(74) Attorney, Agent, or Firm—Panitch Schwarze Belisario & Nadel LLP

(57) ABSTRACT

The inventions provides a method for identifying a target virus in an infected subject comprising the steps of designing a pair of degenerate primers corresponding to highly conserved regions of the target virus; designing a pair of species-specific primers according to highly variable sequences within the conserved regions of the target virus; preparing the species-specific probes according to the larger sequence variations within the conserved regions of the target virus, which are amplified with the species-specific primers as obtained; preparing a test sample by amplifying total nucleic acid of the infected subject with the degenerate primers as obtained; contacting the test sample with the species-specific probes as obtained; and detecting a hybridization between the species-specific probe and the test sample, wherein the hybridization indicates the target virus is identified in the infected subject. The primers and probes for detecting a garget virus are also provided.

12 Claims, 8 Drawing Sheets

| DsMV-P2 | ZaMV-P2 | ZaMMV-P2 | TuMV-P2 | PRSV-P2 | ZYMV-P2 | PVA-P2 | PVY-P2 |
|---------|---------|----------|---------|---------|---------|--------|--------|
| DsMV-P2 | ZaMV-P2 | ZaMMV-P2 | TuMV-P2 | PRSV-P2 | ZYMV-P2 | PVA-P2 | PVY-P2 |
| DsMV-P2 | ZaMV-P2 | ZaMMV-P2 | TuMV-P2 | PRSV-P2 | ZYMV-P2 | PVA-P2 | PVY-P2 |
|         |         |          |         |         |         |        |        |
| DsMV-P3 | ZaMV-P3 | ZaMMV-P3 | TuMV-P3 | PRSV-P3 | ZYMV-P3 | PVA-P3 | PVY-P3 |
| DsMV-P3 | ZaMV-P3 | ZaMMV-P3 | TuMV-P3 | PRSV-P3 | ZYMV-P3 | PVA-P3 | PVY-P3 |
| DsMV-P3 | ZaMV-P3 | ZaMMV-P3 | TuMV-P3 | PRSV-P3 | ZYMV-P3 | PVA-P3 | PVY-P3 |

| DsMV | ZaMV | ZaMMV | TuMV | PRSV | ZYMV | PVA | PVY |
|------|------|-------|------|------|------|-----|-----|
| DsMV | ZaMV | ZaMMV | TuMV | PRSV | ZYMV | PVA | PVY |
| DsMV | ZaMV | ZaMMV | TuMV | PRSV | ZYMV | PVA | PVY |

| DsMV-P2 | PRSV-P2 | PVY-P2 | TuMV-P2 | ZaMV-P2 | ZYMV-P2 |
| --- | --- | --- | --- | --- | --- |
| DsMV-P2 | PRSV-P2 | PVY-P2 | TuMV-P2 | ZaMV-P2 | ZYMV-P2 |
| DsMV-P3 | PRSV-P3 | PVY-P3 | TuMV-P3 | ZaMV-P3 | ZYMV-P3 |
| DsMV-P3 | PRSV-P3 | PVY-P3 | TuMV-P3 | ZaMV-P3 | ZYMV-P3 |

ZaMV + ZaMMV + TuMV

ZaMV + ZaMMV + TuMV

PCPR1/PNIbF1    PCPR1/PNIbF5

PRSV
+
ZYMV

PCPR1/PNIbF1

TuMV
+
ZaMV

SPECIES-SPECIFIC PROBES FOR IDENTIFICATION OF TARGET VIRUS AND IDENTIFICATION METHOD USING SAID PROBES

BACKGROUND OF THE INVENTION

Recent years have seen improved control of some plant virus diseases but increased prevalence of others, fuelled in part by international movement of plant material carrying non-indigenous vectors, and increased resistance of vectors to pesticides. In contrast, the science of plant virology has advanced rapidly with the aid of user-friendly molecular biological procedures, reverse genetics and modern approaches to cell biology.

Conventionally, serological methods especially enzyme-linked immunosorbent assay (ELISA) have been used widely and successfully for detection of plant viruses and diagnosis of plant viral diseases. The nucleic acid-based methods such as reverse transcription (RT) and the polymerase chain reaction (PCR) have recently been used in tool such as microarray to detect plant virus (Bodrossy and Sessitsch, 2004, Current Opinion in Microbiology 7: 245-254; Bryant et al., 2004, The Lancet Infectious Diseases 4: 100-111). Accordingly, several degenerate primers have been designed to recognize the conserved regions of viral genomes of many virus species or the whole virus genus or family (Rose et al., 1998, Nucleic Acid Research 26: 1628-1635).

While it is possible to detect many viruses of the same genus or family by performing RT-PCR given that the genetic sequence of the virus is known, a specific unknown virus species is not effectively distinguished with the currently available technique.

BRIEF SUMMARY OF THE INVENTION

An aspect of the invention provides probes for identifying a target virus species, comprising a first pair of primers corresponding to highly conserved regions of the target virus, which are used for preparing the test sample; a second pair of primers according to the highly variable sequences within the highly conserved regions of the target virus, which are used for designing species-specific probes; and species-specific probes according to the highly variable sequences within the highly conserved regions, which are amplified with the second pair.

Another aspect of the invention provides a method for identifying a target virus in an infected subject comprising the steps of
(i) designing a pair of degenerate primers corresponding to highly conserved regions of the target virus;
(ii) designing a pair of species-specific primers according to highly variable sequences within the conserved regions of the target virus;
(iii) preparing the species-specific probes according to the larger sequence variations within the conserved regions of the target virus, which are amplified with the species-specific primers as obtained in step (ii);
(iv) preparing a test sample by amplifying total nucleic acid of the infected subject with the degenerate primers as obtained in step (i);
(v) contacting the test sample with the species-specific probes as obtained in step (iii); and
(vi) detecting a hybridization between the species-specific probe and the test sample, wherein the hybridization indicates the target virus is identified in the infected subject.

A further aspect of the invention provides a primer pair for detecting potyviruses, which comprises a forward degenerate primer selected from a group consisting of:

```
PNIbF0:
5'AGAGGNAAYAAYAGYGGNCARCC3',      (SEQ ID NO: 1)

PNIbF1:
5'GGBAAYAATAGTGGNCAACC3'          (SEQ ID NO: 27)
and

PNIbF5:
5'GCCAGCCCTCCACCGTNGTNGAYAA3',    (SEQ ID NO: 28)
``` and a reverse degenerate primer comprising:
PCPR1: 5'GGGGAGGTGCCGTTCTCDATRCACCA3' (SEQ ID NO: 2), wherein R is adenine (A) or guanine (G), Y is C or thymine (T), B is C, G or T, D is A, G or T, and N is A, C, G or T.

In accordance with yet another aspect, the invention provides a method for detecting potyviruses in a plant, which comprises amplifying total RNA of the plant with a forward degenerate primer selected from a group consisting of

```
PNIbF0:
5'AGAGGNAAYAAYAGYGGNCARCC3',      (SEQ ID NO: 1)

PNIbF1:
5'GGBAAYAATAGTGGNCAACC3'          (SEQ ID NO: 27)
and

PNIbF5:
5'GCCAGCCCTCCACCGTNGTNGAYAA3',    (SEQ ID NO: 28)
``` and a reverse degenerate primer comprising:
PCPR1: 5'GGGGAGGTGCCGTTCTCDATRCACCA3' (SEQ ID NO: 2), wherein R is adenine (A) or guanine (G), Y is C or thymine (T), B is C, G or T, D is A, G or T, and N is A, C, G or T to obtain an amplified product. The amplified product is then analyzed. And the plant is infected with the potyviruses if the amplified product has a molecular size of about 1.0 kb to about 1.2 kb.

One other aspect of the invention provides a method for identifying a potyvirus species, which comprises preparing a test sample through amplifying total RNA of a test subject with a forward degenerate primer selected from a group consisting of

```
PNIbF0:
5'AGAGGNAAYAAYAGYGGNCARCC3',      (SEQ ID NO: 1)

PNIbF1:
5'GGBAAYAATAGTGGNCAACC3'          (SEQ ID NO: 27)
and

PNIbF5:
5'GCCAGCCCTCCACCGTNGTNGAYAA3',    (SEQ ID NO: 28)
``` and a reverse degenerate primer comprising:
PCPR1: 5'GGGGAGGTGCCGTTCTCDATRCACCA3' (SEQ ID NO: 2), wherein R is adenine (A) or guanine (G), Y is C or thymine (T), B is C, G or T, D is A, G or T, and N is A, C, G or T, and contacting the test sample with species-specific probes. And the potyvirus species is identified when the test sample is hybridized with the potyvirus species-specific probes.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 4A is a schematic diagram illustrating locations of the species-specific cDNA probes according to one embodiment of the invention.

FIG. 4B is a dot blot image showing the targets hybridized with the species-specific cDNA probes arranged according to FIG. 4A.

FIG. 6A is a schematic diagram illustrating locations of the species-specific cDNA probes on a dot blot image according to one other embodiment of the invention;

FIG. 6B is dot blot image showing the targets hybridized with the species-specific cDNA probes arranged according to FIG. 6A;

FIG. 7A is dot blot image showing the mix-infected targets hybridized with the species-specific cDNA probes according to another embodiment of the invention;

FIG. 7B is dot blot image showing the mix-infected targets hybridized with the species-specific oligonucleotide probes according to another embodiment of the invention; and FIGS. 8A and 8B are dot blot images showing the mix-infected targets hybridized with the species-specific cDNA probes according to a further embodiment of the invention.

DETAILED DESCRIPTION OF THE INVENTION

To facilitate the understanding of the invention, a number of terms are defined below.

A "primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions.

Figure 1A:
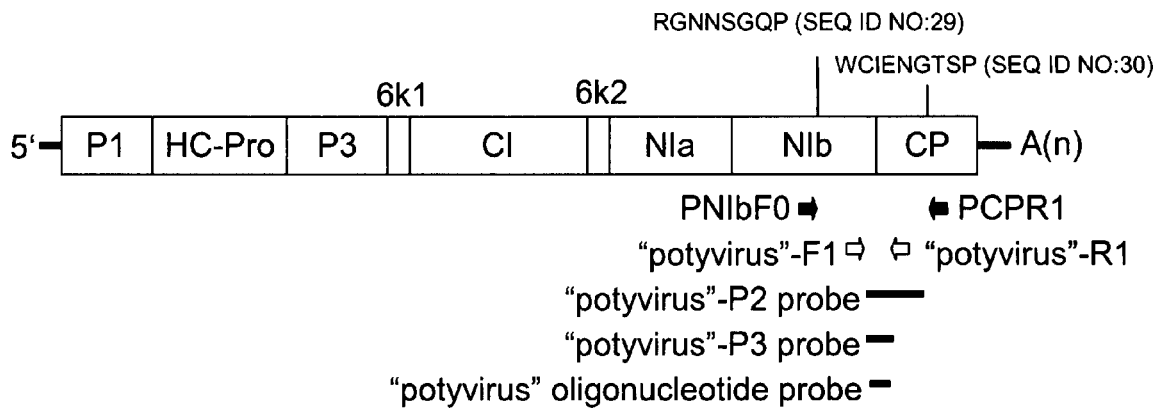
FIGS. 1A and 1B are schematic diagrams illustrating locations of the primers and probes according to the present invention, wherein the solid arrows represent degenerate primers of *Potyvirus* genus, hollow arrows represent species-specific primers, and solid lines represent cDNA probes (P2 probe and P3 probe) and oligonucleotide probes respectively.

A "highly conserved region" herein refers to a section of consensus gene or amino acid sequence relatively invariable or "conserved" as compared to other sections of the sequence among a number of species of the same genus. For example, CP region and NIb region as shown in FIG. 1A are highly conserved regions in the potyvirus genome.

A "test sample" as used herein refers to a test subject's amplified genetic material such s amplified total nucleic acid of a test subject from which a target virus species is detected or identified. For example, total RNA (ribonucleic acid) of a plant is one type of the test sample described in the invention.

The present invention provides a method for preparing species-specific probes of a target virus. The method comprises steps of designing a first pair of primers corresponding to highly conserved regions of the target virus, designing a second pair of primers according to highly variable sequences within the highly conserved regions of the target virus, and preparing the species-specific probes according to highly variable sequences within the highly conserved regions.

In the design of the first pair of primers or degenerate primers, the conserved region is determined by aligning amino acid sequences of a plurality of viruses or members in the genus of target virus. The amino acid sequences of the viruses may be collected from the sequence databases using LOOKUP program in SeqWeb (Accelrys Inc., San Diego, Calif., USA). As the amino acid sequences of the viruses are aligned by sequence-aligning program in SeqWeb, several conserved regions are located to further determine the highly conserved regions in the target virus.

In accordance with one embodiment of the invention, the method comprises steps of designing the first pair of primers corresponding to highly conserved regions of the target virus, designing the second pair of primers according to larger sequence variations within the highly conserved regions of the target virus, and preparing the species-specific oligonucleotide probes according to larger sequence variations within the highly conserved regions complementary to the second pair of primers.

In accordance with another embodiment of the invention, the method comprises steps of designing the first pair of primers corresponding to highly conserved regions of the target virus, designing the second pair of primers according to larger sequence variations within the highly conserved regions of the target virus, and preparing species-specific cDNA probes by amplifying the gene sequence of the target virus with the second pair of primers.

In one preferred embodiment, the target virus may be a potyvirus species. And the first pair of primers comprises a forward degenerate primer selected from a group consisting of PNIbF0:
5'AGAGGNAAYAAYAGYGGNCARCC3',  (SEQ ID NO: 1)

-continued

PNIbF1:
5'GGBAAYAATAGTGGNCAACC3'   (SEQ ID NO: 27)
and

PNIbF5:
5'GCCAGCCCTCCACCGTNGTNGAYAA3',   (SEQ ID NO: 28)

and a reverse degenerate primer comprising

PCPR1: 5'GGGGAGGTGCCGTTCTCDATRCACCA3' (SEQ ID NO: 2), wherein R is adenine (A) or guanine (G), Y is C or thymine (T), B is C, G or T, D is A, G or T, and N is A, C, G or T.

The potyviruses species includes but is not limited to Dasheen mosaic virus (DsMV), Papaya ringspot virus (PRSV), Potato virus A (PVA), Potato virus Y (PVY), Turnip mosaic virus (TuMV), Zantedeschia mosaic virus (ZaMV), Zantedeschia mild mosaic virus (ZaMMV) and Zucchini yellow mosaic virus (ZYMV).

Therefore, in a preferred embodiment, the second pair of primers or species-specific primers comprising DsMV-F1 of SEQ ID NO: 3, DsMV-R1 of SEQ ID NO: 11, PRSV-F1 of SEQ ID NO: 4, PRSV-R1 of SEQ ID NO: 12, PVA-F1 of SEQ ID NO: 5, PVA-R1 of SEQ ID NO: 13, PVY-F1 of SEQ ID NO: 6, PVY-R1 of SEQ ID NO: 14, TuMV-F1 of SEQ ID NO: 7, TuMV-R1 of SEQ ID NO: 15, ZaMV-F1 of SEQ ID NO: 8, ZaMV-R1 of SEQ ID NO: 16, ZaMMV-F1 of SEQ ID NO: 9, ZaMMV-R1 of SEQ ID NO: 17, ZYMV-F1 of SEQ ID NO: 10 and ZYMV-R1 of SEQ ID NO: 18. The detailed sequences of the first and second pairs of primers are listed in Table 1 below.

TABLE 1

| Primer[a] | Sequence[b] |
|---|---|
| potyvirus degenerate primer | |
| PNIbF0 (SEQ ID NO: 1) | 5'AGAGGNAAYAAYAGYGGNCARCC3' |
| PNIbF1 (SEQ ID NO: 27) | 5'GGBAAYAATAGTGGNCAACC3' |
| PNIbF5 (SEQ ID NO: 28) | 5'GCCAGCCCTCCACCGTNGTNGAYAA3' |
| PCPR1 (SEQ ID NO: 2) | 5'GGGGAGGTGCCGTTCTCDATRCACCA3' |
| "potyvirus"-F1 primer | |
| DsMV-F1 (SEQ ID NO: 3) | 5'AAATGTGAAGGAGTGCGAACTTCA3' |
| PRSV-F1 (SEQ ID NO: 4) | 5'AGTAAGCGTGGGTCAATGGA3' |
| PVA-F1 (SEQ ID NO: 5) | 5'TCTATCCAGTTTGATGAACAAATGG3' |
| PVY-F1 (SEQ ID NO: 6) | 5'TGGATGAGGAAGAGCTGAGAG3' |
| TuMV-F1 (SEQ ID NO: 7) | 5'CCAGCTCAAGAAGATCTTACTC3' |
| ZaMV-F1 (SEQ ID NO: 8) | 5'TCGTGATGCTAATGAGGAGGAG3' |
| ZaMMV-F1 (SEQ ID NO: 9) | 5'CTCACATATGATGAGGATGGGG3' |
| ZYMV-F1 (SEQ ID NO: 10) | 5'ACTGGCACGATACCTACAAGC3' |
| "potyvirus"-R1 primer | |
| DsMV-R1 (SEQ ID NO: 11) | 5'AACTTCCTTGCCTTTCTCACTTG3' |
| PRSV-R1 (SEQ ID NO: 12) | 5'CTCTCCAGTTTTTGTGCTAGTTG3' |
| PVA-R1 (SEQ ID NO: 13) | 5'TTCACGGCTACAGCTTTGCTAC3' |
| PVY-R1 (SEQ ID NO: 14) | 5'TGTTCGGGTTTGACTGGATGCT3' |
| TuMV-R1 (SEQ ID NO: 15) | 5'TCGCGTTCACCCTCTTCTTG3' |
| ZaMV-R1 (SEQ ID NO: 16) | 5'GTGTGTTTGCACTTGTTTGTTC3' |
| ZaMMV-R1 (SEQ ID NO: 17) | 5'CAGATCTCTTTGGCCTTGGGTT3' |
| ZYMV-R1 (SEQ ID NO: 18) | 5'CTTGGCAGCTACTACTGTTTTC3' |

[a]F0, F1 and F5 indicate forward primers, whereas R1 indicates reverse primer.
[b]Nucleotide at degenerate positions are represented by a single letter code;
R = A and G; Y = C and T; B = C, G and T; D = A, G and T; N = A, C, G and T.

And based on the potyviruses species described above, the species-specific oligonucleotide probes may be selected from a group consisting of DsMV-O1 of SEQ ID NO: 19, PRSV-O1 of SEQ ID NO: 20, PVA-O1: of SEQ ID NO: 21, PVY-O1 of SEQ ID NO: 22, TuMV-O1 of SEQ ID NO: 23, ZaMV-O1 of SEQ ID NO: 24, ZaMMV-O1 of SEQ ID NO: 25 and ZYMV-O1 of SEQ ID NO: 26. The detailed sequences of the species-specific oligonucleotide probes are listed in Table 2 below.

TABLE 2

| probe | sequence |
|---|---|
| DsMV-O1 (SEQ ID NO:19) | 5'GCGATATTTGGATGCTTTCAACTTTGAGTTATTC TGTGAGCATGATGAAG3' |
| PRSV-O1 (SEQ ID NO:20) | 5'GTAGATAAATATTTTGAGCGAGAAAGGGGAGATT CACCTGAGCTACTGGT3' |
| PVA-O1 (SEQ ID NO:21) | 5'TCTATCCAGTTTGATGAACAAATGGATGAAGAAG ATGACATGGTGTATTT3' |
| PVY-O1 (SEQ ID NO:22) | 5'AGAGCCTTCACTGAAATGATGGTCGCATTAGACG ATGAGTTTGAATTTGA3' |
| TuMV-O1 (SEQ ID NO:23) | 5'GCAATCTTTGAGGATTATGAAGACGGTACTGAGA CTTGTGTTTATCACCA3' |
| ZaMV-O1 (SEQ ID NO:24) | 5'CTAAGGTATGCCACTGAACAGAGCATTGAATGGC CACAGGAGGAACAAGT3' |
| ZaMMV-O1 (SEQ ID NO:25) | 5'TGTTGAAGTCCTCACATATGATGAGGATGAGGGG TGTGGCGAGGATGTCG3' |
| ZYMV-O1 (SEQ ID NO:26) | 5'CCTCCATCAAGATATCTTCTTTGAACAAGGAGAC ACTGTAATGCTCCAAT3' |

The invention also provides a method for identifying a target virus species. The method comprises steps of preparing a test sample by amplifying a test subject's total nucleic acid with a first pair of primers corresponding to highly conserved regions of the target virus, and contacting the test sample with species-specific probes of the target virus. And the target virus species is identified if the test sample is hybridized with the species-specific probes of the target virus.

In accordance with one preferred embodiment, a method for identifying the potyvirus species may be provided. The degenerate primers (Table 1) are used for amplifying the total nucleic acid of a test subject, such as total RNA of a test plant in RT-PCR. With species-specific cDNA probe or species-specific oligonucleotide probe (Table 2) corresponding to individual potyviruses, a reverse dot blot hybridization is performed for contacting the test sample with the species-specific probes. And the potyvirus species is identified if the test sample is hybridized with the species-specific probes. The species-specific cDNA probe is prepared by amplifying the virus selective clone with the species-specific primers (Table 1) in PCR, and the species-specific oligonucleotide probe is designed according to a synthetic oligonucleotide sequence.

Also, the invention provides a method for detecting the genus of target virus in a plant. As the first pair of primers is specific to the genus of target virus, it is used to amplify a test sample, such as total RNA of the plant in reverse transcription polymerase chain reaction (RT-PCR). Then, the plant is detected for any infection with members in the genus of the target virus by analyzing an RT-PCR product.

The invention also provides a method for detecting potyviruses in a plant. The method comprises steps of amplifying total RNA of the plant with primers selected from a group consisting of:

```
PNIbF0:
5'AGAGGNAAYAAYAGYGGNCARCC3',      (SEQ ID NO: 1)

PNIbF1:
5'GGBAAYAATAGTGGNCAACC3'          (SEQ ID NO: 27)
and

PNIbF5:
5'GCCAGCCCTCCACCGTNGTNGAYAA3',    (SEQ ID NO: 28)
and

PCPR1:
5'GGGGAGGTGCCGTTCTCDATRCACCA3',   (SEQ ID NO: 2)
``` wherein R is adenine (A) or guanine (G), Y is C or thymine (T), B is C, G or T, D is A, G or T, and N is A, C, G or T to obtain an amplified product. The amplified product is then analyzed in an assay, such as 1% agarose gel electrophoresis. And the plant is said to be infected with the potyviruses of the same genus if the amplified product has a molecular size of about 1.0 kb to about 1.2 kb.

According to the method for detecting potyviruses, the degenerate primers are used in the RT-PCR. The non-dT primer (such as PCPR1 primer) is used for reverse transcription of the total RNA of the plant to prevent interaction with the poly(A)$^+$ mRNA of the plant. The RT-PCR is performed using non-dT primer as the reverse transcription primer to obtain a product that is less likely a non-specific fragment. Therefore, the potyviruses of the same genus can be detected quickly with the method adopting the degenerate primers in the RT-PCR.

According to one embodiment, total RNA is extracted from the plant infected with virus, such as Dasheen mosaic virus (DsMV), Papaya ringspot virus (PRSV), Potato virus A (PVA), Potato virus Y (PVY), Turnip mosaic virus (TuMV), *Zantedeschia* mosaic virus (ZaMV), *Zantedeschia* mild mosaic virus (ZaMMV) and Zucchini yellow mosaic virus (ZYMV) respectively. The total RNA is amplified by performing RT-PCR with PCPR1 as a RT primer, and PCPR1 and PNIbF0 as PCR primers. Next, the RT-PCR product is analyzed to detect the potyviruses in the infected plant.

In another embodiment, the total RNA is extracted from the plants infected with virus, such as DsMV, ZaMV, TuMV, PRSV, ZYMV and PVY respectively. The total RNA is amplified by performing RT-PCR with PCPR1 as a RT primer, and PCPR1, PNIbF1 and PNIbF5 as PCR primers. The RT-PCR product is analyzed to determine the potyviruses in the infected plant.

In one preferred embodiment, two cDNA probes "potyvirus"-P2 probe and "potyvirus"-P3 probe are prepared by amplifying eight potyvirus selective clones, such as DsMV, ZaMV, ZaMMV, TuMV, PRSV, ZYMV, PVA and PVY in PCR. Next, the P2 and P3 probes are immobilized on a nylon membrane. Alternatively, the oligonucleotide probes are diluted by water and immobilized on the nylon membrane. In addition, a test sample is prepared by amplifying total RNA extracted from the plant infected with DsMV, ZaMV, ZaMMV, TuMV, PRSV, ZYMV, PVA and PVY with the degenerate primer pair (PCPR1/PNIbF0) for detecting the potyviruses in RT-PCR. The test sample is then PCR-labeled with digoxigenin (DIG) and subjected to reverse dot blot hybridization on the nylon membrane above.

In another embodiment, two cDNA probes "potyvirus"-P2 probe and "potyvirus"-P3 probe are prepared by amplifying six potyvirus selective clones, such as DsMV, PRSV, PVY, TuMV, ZaMV and ZYMV in PCR. Next, the P2 and P3 probes are immobilized on a nylon membrane. In addition, the test sample is prepared by amplifying total RNA extracted from the plant infected with DsMV, PRSV, PVY, TuMV, ZaMV and ZYMV with the degenerate primer pair PCPR1/PNIbF1 or PCPR1/PNIbF5 for detecting the potyviruses in RT-PCR. The test sample is then PCR-labeled with digoxigenin (DIG) and subjected to reverse dot blot hybridization on the nylon membrane above.

In a further embodiment, the plant which is simultaneously infected with ZaMV, ZaMMV and TuMV is screened by ELISA. The total RNA of the plant is then extracted to identify potyvirus species. And regardless of whether the nylon membrane is immobilized with the cDNA or oligonucleotide probes, all the potyvirus species involved in the mixed infection are identified by hybridizing the test sample with the species-specific probes in a reverse dot blot hybridization reaction.

According to another embodiment, plant which is simultaneously infected with PRSV and ZYMV or TuMV and ZaMV is screened by ELISA. The total RNA of the plant is then extracted to identify the potyvirus species. And all the potyvirus species involved in the mixed infection are identified by hybridizing the test sample with the cDNA probes immobilized on the nylon membrane in a reverse dot blot hybridization reaction.

Since the species-specific cDNA probe and species-specific oligonucleotide probe are immobilized on the nylon membrane, the method for identifying the potyvirus species may be applicable to a membrane array type chip or biological chip to quickly identify the potyvirus species. And since the oligonucleotide probe is prepared without producing viral cDNA selective clone, the chance of producing false positive result is minimized. Therefore, it is a future trend to apply the oligonucleotide probe in the development of biological detection chip for effectively detecting and identifying the target virus species.

For example, a kit may be provided for identifying potyvirus species, which comprises the forward degenerate primer selected from a group consisting of:

```
PNIbF0:
5'AGAGGNAAYAAYAGYGGNCARCC3',     (SEQ ID NO: 1)

PNIbF1:
5'GGBAAYAATAGTGGNCAACC3'         (SEQ ID NO: 27)
and

PNIbF5:
5'GCCAGCCCTCCACCGTNGTNGAYAA3',   (SEQ ID NO: 28)
``` the reverse degenerate primer comprising:

PCPR1: 5'GGGGAGGTGCCGTTCTCDATRCACCA3' (SEQ ID NO: 2), wherein R is adenine (A) or guanine (G), Y is C or thymine (T), B is C, G or T, D is A, G or T, and N is A, C, G or T, and a nylon membrane immobilized with the species-specific probes.

Accordingly, a standard operation procedure can be provided by combining the method for detecting target virus genus and the method for identifying target virus species to quickly detect and identify target virus genus and target virus species.

Summarizing from the above, it is understood that the present invention provides a method for preparing the species-specific probe of a target virus. The invention also provides a method for identifying a target virus species. Specifically, the invention also applies to identification and detection of the potyvirus species or genus. And the methods are widely applicable to detecting and identifying other virus types, such as human viruses, animal viruses and so on, without limiting to specific virus types as embodied and in the example below.

For example, if other unknown viruses of the genus χ virus are to be explored, the χ virus degenerate primers are designed based on sequence alignment result in the sequence database. Next, PCR or RT-PCR is performed using the degenerate primers to design species-specific primers after cloning, sequencing and sequence alignment. The species-specific cDNA probes or species-specific oligonucleotide probe of the target virus is prepared. A test sample is prepared by amplifying total nucleic acid of a test subject, such as total RNA of the plant with the degenerate primers in PCR or RT-PCR. The test sample is allowed to hybridize with the species-specific cDNA probe or species-specific oligonucleotide probe for the genus χ virus in the reverse dot blot hybridization. And the hybridization result is analyzed. Therefore, the present invention also provides a method for identifying a target virus in an infected subject comprising steps:

(i) designing degenerate primers corresponding to highly conserved reions of the target virus;

(ii) designing species-specific primers according to highly variable sequences within the conserved regions of the target virus;

(iii) preparing the species-specific probes according to larger sequence variations within the conserved regions, which are amplified with the species-specific primers as obtained in step (ii);

(iv) preparing a test sample by amplifying total nucleic acid of the infected subject with the degenerate primers as obtained in step (i);

(v) performing a reverse dot blot hybridization between the test sample and a nylon membrane immobilized with the species-specific probes as obtained in step (iii); and (vi) detecting a hybridization between the species-specific probe and the test sample, wherein the hybridization indicates the target virus is identified in the infected subject.

The invention will now be described in further detail with reference to the following specific, non-limiting examples.

Material and Methods

1. Virus Sources

Eight different potyviruses, one cucumovirus, one potexvirus, two carmoviruses and two tobamoviruses were used in this study. A potato isolate of potato virus A (PVA), a potato isolate of potato virus Y (PVY) and a radish isolate of Turnip mosaic virus (TuMV) were kindly supplied by Dr. Tso-Chi Yang (Taiwan Seed Improvement and Propagation Station, Council of Agriculture) as dehydrated infected leaf tissues. The PVA and PVY were inoculated and maintained in *Nicotiana tabacum* var. Samsun and TuMV in radish (*Raphanus sativus*), respectively. Tomato bushy stunt virus (TBSV) was supplied by Dr. T. Jack Morris (School of Biological Sciences, University of Nebraska, Lincoln, USA) and inoculated and maintained in *N. benthamiana*. The remaining viruses are collections in Applicant's laboratory (Department of Plant Pathology and Microbiology, National Taiwan University). ZAN isolate of Dasheen mosaic virus (DsMV), ZAN isolate of *Zantedeschia* mosaic virus (ZaMV) (Chang et al., 2001, Pant Disease 85:1289), and *Zantedeschia* mild mosaic virus (ZaMMV) originally from calla lily (*Zantedeschia* spp.) were separately maintained in *Philodendron selloum*. A papaya isolate of Papaya ringspot virus (PRSV) and a loofah isolate of Zucchini yellow mosaic virus (ZYMV) collected from the experimental farm of National Taiwan University were maintained in papaya (*Carica papaya*) and zucchini squash (*Cucurbita pepo*), respectively. Cucumber mosaic virus (CMV) (isolated from New Guinea impatiens), Tobacco mosaic virus (TMV) (isolated from tobacco) and Tobacco mild green mosaic virus (TMGMV) (isolated from chilli) were maintained in *N. benthamiana*. Cymbidium mosaic virus (CymMV) (isolated from orchid) was maintained in orchid (*Phalaenopsis* spp.). And Hibiscus chlorotic ringspot virus (HCRSV) (isolated from hibiscus) was maintained in kenaf (*Hibiscus cannabinus*).

2. Plant Total RNA Extraction

Leaf tissue (100 mg) was harvested and ground into fine powder in liquid nitrogen, and then transferred to a microfuge tube. Plant total RNAs were extracted from pulverized tissue according to the protocol of Plant Total RNA Extraction Miniprep System (Viogene, Calif., USA).

3. Degenerate Primer Design

Figure 1B:
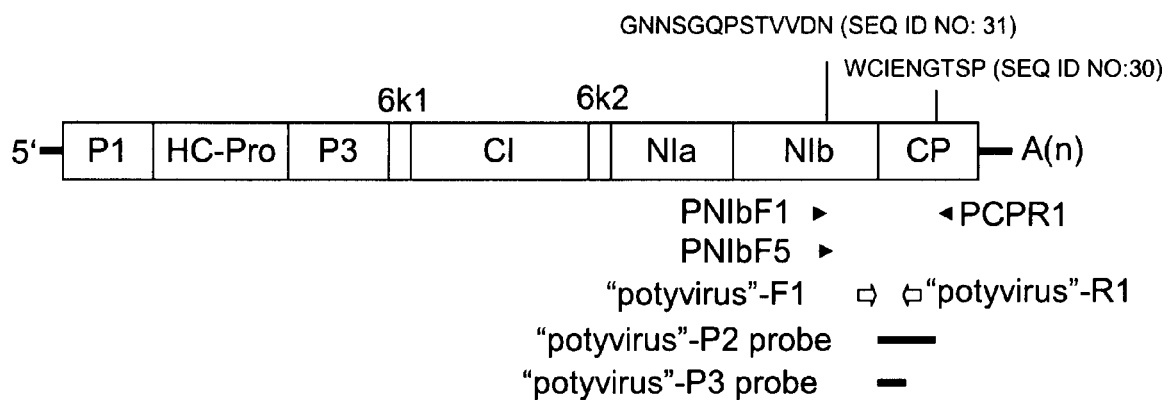

The amino acid sequences of potyviruses were collected from the PIR and Swiss-Prot databases using LOOKUP program in Seq Web (Acceirys Inc., San Diego, CA, USA). Thirty-three sequences were aligned by PILEUP and PRETTY program in SeqWeb. Several conserved regions were found and the consensus sequence was transferred to the CODEHOP web site blocks.fhere.org/blocks/codehop.html (Rose et al., 1998, Nucleic Acids Research 26: 1628-1635). The consensus sequence was first pasted on the multiple alignment processor as FASTA format, then it was reformatted into Blocks Database format by the multiple alignment processor. The Blocks were then used to design the degenerate primers with the temperature setting at 60° C. and the codon usage table setting at equal. For the degenerate primers located in the CP region, several suggested primers were obtained and one, which had the lowest degeneration, was selected as the reverse degenerate primer: PCPR1 (Table 1) to correspond to the conserved sequence WCIENGTSP (SEQ ID NO:30) (FIG. 1A). A similar approach was used to design forward degenerate primers: PNIbF0, PNIbF1 and PNIbF5 (Table 1) corresponding to a conserved sequence in the NIb region encoding the amino acid sequences RGNNSGQP (SEQ ID NO:29), GNNSGQP (SEQ ID NO:32) and GQPSTVVDN (SEQ ID NO:33), respectively, wherein GNNSGQP (SEQ ID NO:32) and GQPSTVVDN (SEQ ID NO:33) were based on the conserved seciuence GNNSGQPSTVVDN (SEQ ID NO:31) (FIGS. 1A and 1B).

4. RT-PCR Amplification of Viral RNA

For RT reaction, 0.35 μg of plant total RNA and 50 pmol PCPR1 primer were added into a microfuge tube, incubated at 65° C. for 10 min and then kept on ice for 5 min. The cDNA synthesis reaction was carried out in a total volume of 50 μl using AMV reverse transcriptase (Promega, Wis., USA) according to the manufacture's instructions. The PCR reaction required 2 μl of RT product, 5 pmol PCPR1 primer, 5 pmol PNIbF0, PNIbF1 or PNIbF5 primer, 4 nmol dNTPs, 1 U DyNAzyme™ II DNA polymerase (Finnzymes Inc., Finland), 1X DyNAzyme™ II DNA polymerase buffer in a total volume of 20 μl. The PCR reaction was carried out using GeneAmp® PCR system 2400 or 9700 (Perkin-Elmer Applied Biosystems, CA, USA) and an initial incubation at 94° C. for 5 min was followed by 35 cycles at 94° C. for 30 s, 55° C. for 45 s and 72° C. for 1 min, and a final incubation at 72° C. for 7 min.

5. Cloning and Sequencing of cDNA Fragments of Different Potyviruses

RT-PCR products derived from each potyvirus were examined in 1% agarose gel and purified by GFX™ PCR DNA and Gel Band Purification Kit (Amersham Pharmacia Biotech, NJ, USA). The products were cloned into the pGEM-T® Easy vector (Promega, Wis., USA). The ligation reaction was set up as suggested by the technical manual, and the products were used to transform E. coli DH5α. Recombinant colonies were detected by blue-white selection (Sambrook and Russell, 2001, A Laboratory Manual, 3rd edition, Cold Spring Harbor Laboratory Press) and colony PCR.

All clones were sequenced using the ABI PRISM® BigDye™ terminator cycle sequencing ready reaction kit (Perkin-Elmer Applied Biosystems, CA, USA) and T7 and SP6 primers separately. The sequencing PCR reaction was carried out according to the manufacturer, and clones were sequenced using the ABI PRISM® 310 genetic analyzer (Perkin-Elmer Applied Biosystems, CA, USA).

6. Sequence Analysis

Sequence analysis was undertaken using the Wisconsin GCG package version 10.3 and SeqWeb version 1.2 (Accelrys Inc., San Diego, Calif., USA). The sequences were assembled by the Fragment Assembly System (FAS) and analyzed through similarity search by BLAST and FASTA programs in Wisconsin package. The amino acid sequences were aligned using the PILEUP and PRETTY programs in SeqWeb.

7. Species-Specific Probe Preparation and Immobilization

The amino acid sequences of the NIb and CP of the eight potyviruses were aligned to facilitate the design of species-specific primer pairs for each of the eight potyviruses (Table 1). The primers were located in a variable region between the 3' end of the NIb gene and the 5' end of the CP gene (FIG. 1A). The species-specific probes for each virus were prepared by PCR amplification of the corresponding viral cDNA clone. Two probes that contain the variable region were prepared for each virus. The "potyvirus"-P2 probes (FIG. 1A) started from the species-specific forward primer ("potyvirus"-F1, Table 1) and ended at PCPR1 primer; their sizes ranged from 466 base pairs (bp) to 600 bp. The "potyvirus"-P3 probes (FIG. 1A) started from the species-specific forward primer but ended at the species-specific reverse primer ("potyvirus"-R1, Table 1). The probe sizes ranged between 171 and 313 bp.

After gel electrophoresis, the concentration of each probe was measured by the Kodak Digital Science™ 1D image analysis software (Eastman Kodak Company, NY, USA), and then adjusted to 10 ng/μl before application. The probes were denatured at 94° C. for 10 min, and then chilled on ice for 5 min. The probes (0.3 μl to 0.5 μl) were transferred to the nylon membrane. The membrane was air-dried before carrying out UV cross-linking to immobilize the probes.

The species-specific oligonucleotide probes were also located in a variable region between the 3' end of the NIb gene and the 5' end of the CP gene (FIG. 1A). A 50 mer oligonucleotide probe for each virus was designed and prepared by the manufacturer based on the sequence variations of eight potyviruses DsMV, PRSV, PVA, PVY, TuMV, ZaMV, ZaMMV and ZYMV after being sequenced and aligned according to the Potyvirus degenerate primer design described above. The concentration of each viral oligonucleotide probe was adjusted to 100 μM before application. The probes (0.3 μl to 0.5 μl) were transferred to the nylon membrane, the membrane was air-dried, and then UV cross-linking was carried out to immobilize the probes.

8. Test Sample Preparation and Labeling

The test samples were prepared from total RNA and labeled during the PCR. The plant total RNA was amplified in RT-PCR with the primer pairs PCPR1/NIbF0, PCPR1/NIbF1 or PCPR1/NIbF5 as described previously except 200 μM dNTPs was substituted by 1× PCR DIG labeling mix (Roche Applied Science, Mannheim, Germany). The concentration of the test sample was adjusted to 6 ng/μl to 10 ng/μl before use.

9. Reverse Dot Blot Hybridization

The nylon membrane was pre-hybridized with freshly prepared hybridization solution [50% formamide, 5×SSC (v/v), 2% blocking reagent (w/v) (Roche Applied Science, Mannheim, Germany), 0.1% N-lauroylsarcosine (w/v), 0.02% SDS (w/v)] at 50° C. for at least 1 hr. The test sample was denatured at 96° C. for 10 min, and chilled on ice for 5 min before the addition of 1 μl to 5 μl test sample per 10 ml hybridization solution. Hybridization was performed at 50° C. for at least 6 hr, after which, the membrane was washed in 2×SSC, 0.1% SDS for 5 min at room temperature twice. The membrane was then washed in 0.1×SSC, 0.1% SDS for 15 min at 68° C. twice. The membrane could be used directly for detection or air-dried for storage.

The membrane was washed briefly in buffer 1 (0.1 M maleic acid, 0.15 M NaCl, pH 7.5), and then incubated in buffer 2 (1% blocking reagent in buffer 1) at room temperature for 30 min. The membrane was incubated in 20 ml diluted antibody-conjugate (Roche Applied Science, Mannheim, Germany; diluted to 75 mU/ml in buffer 2) at room temperature for 30 min. After incubation, the membrane was washed in buffer 1 at room temperature for 15 min twice and then incubated in 1 ml CDP-Star solution (Roche Applied Science, Mannheim, Germany) at room temperature for 15 min. The fluorescent signal was detected by sealing the membrane and exposing on X-ray film.

EXAMPLE 1

Specificity of Potyvirus Degenerate Primers

The total RNA of the plants infected with six different viruses, including cucumovirus (CMV), potexvirus (CymMV), tombusvirus (TBSV), tobamovirus (TMGMV), and potyviruses (PVA and ZYMV), respectively was subjected to RT-PCR analysis using the degenerate primer pair PCPR1/PNIbF0.

Figure 2A:
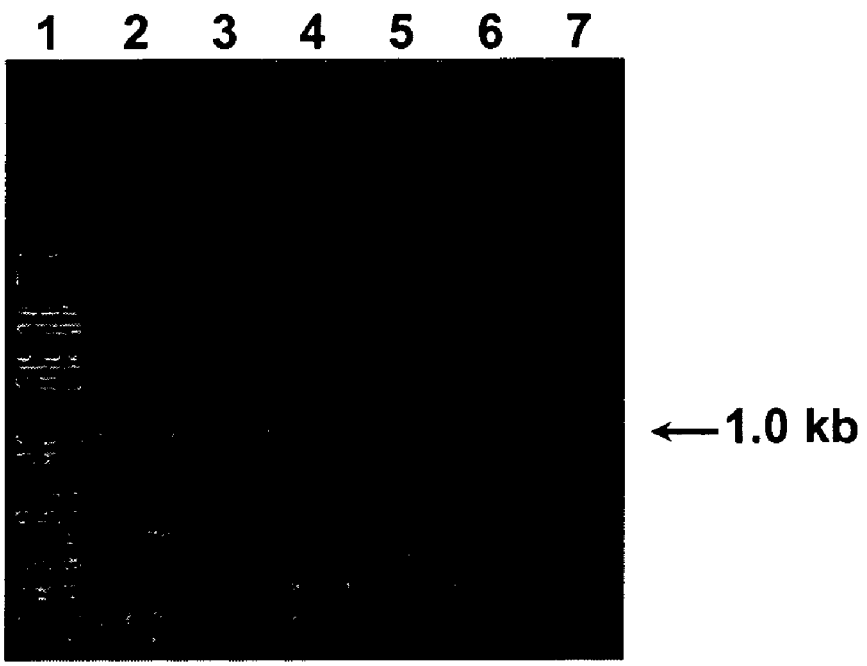
FIG. 2A is an agarose gel image showing RT-PCR product amplified with degenerate primers PCRR1 and PNIbF0.

Referring to FIG. 2A, total RNA of different virus-infected plants was loaded in the 1% agarose gel electrophoresis, wherein lane 1 was loaded with 1 kb plus DNA ladder (Invitrogen, CA, USA), lane 2 was loaded with ZYMV-infected *Cucurbita pepo*, lane 3 was loaded with PVA-infected *Nicotiana benthamiana*, lane 4 was loaded with TMGMV-infected *Nicotiana benthamiana*, lane 5 was loaded with TBSV-infected *Nicotiana benthamiana*, lane 6 was loaded with CymMV-infected *Phalaenopsis* spp. and lane 7 was loaded with CMV-infected *Nicotiana benthamiana*.

Accordingly, these primers only generated a specific 1.0-kb RT-PCR product with PVA and ZYMV, they did not amplify any specific product with CMV, CymMV, TBSV and TMGMV (FIG. 2A).

In addition, five viruses belonging to different genus or family were used in RT-PCR tests. The total RNAs were extracted from each virus-infected plants and analyzed by RT-PCR with two pairs of potyvirus degenerate primers PCRR1/PNIbF1 and PCPR1/PNIbF5 (Table 1). These primers corresponded to the conserved sequences located in the NIb and CP regions.

Figure 2B:
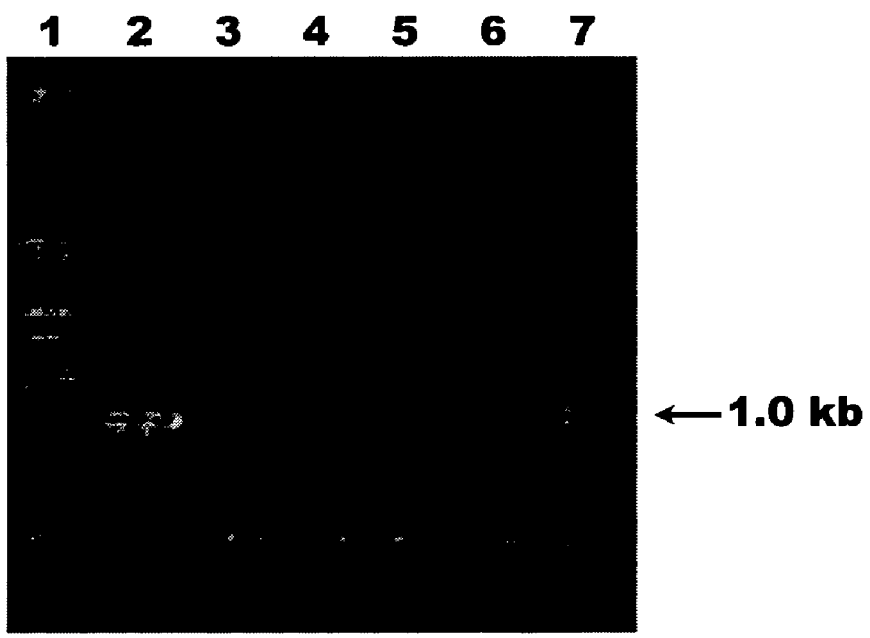
FIG. 2B is an agarose gel image showing RT-PCR product amplified with degenerate primers PCRR1 and PNIbF1.
Figure 2C:
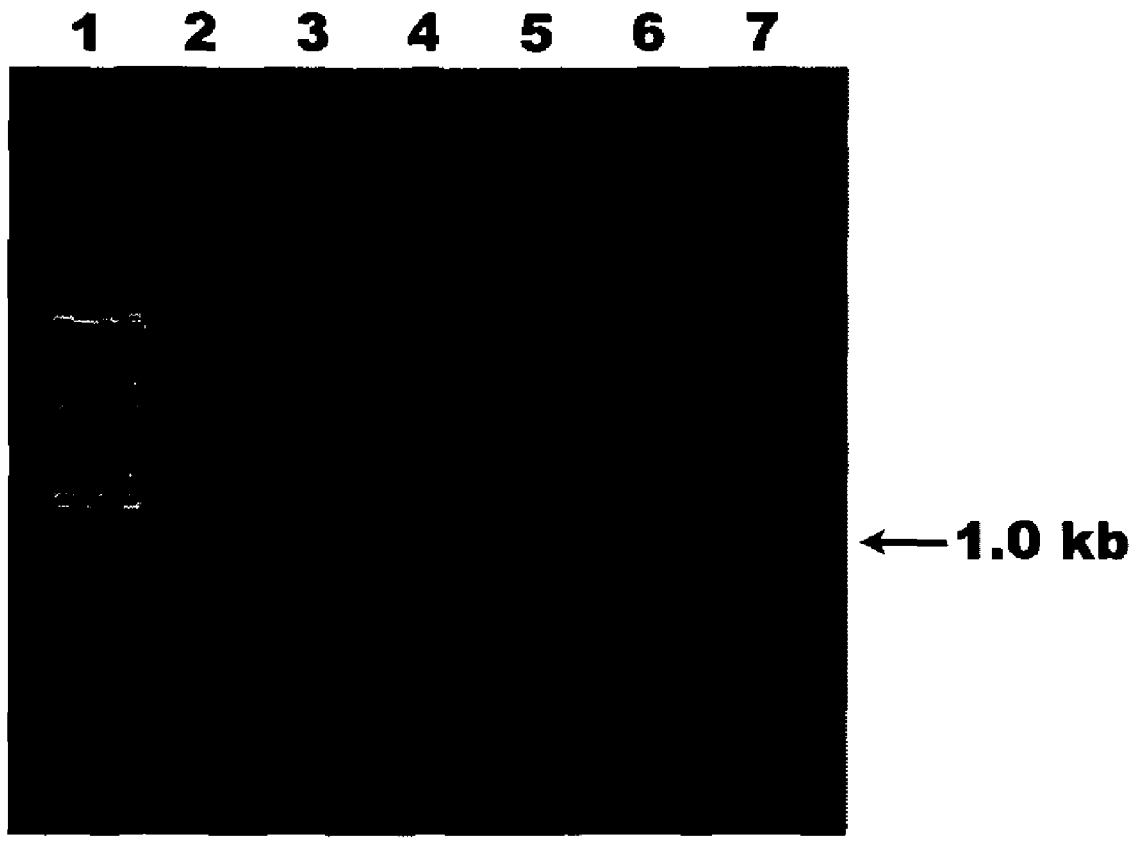
FIG. 2C is an agarose gel image showing RT-PCR product amplified with degenerate primers PCRR1 and PNIbF5.

Referring to both FIGS. 2B and 2C, total RNA of different virus-infected plants was loaded in the 1% agarose gel electrophoresis, wherein lane 1 was loaded with 1 kb plus DNA ladder (Invitrogen, CA, USA), lane 2 was loaded with positive control (cDNA clone of ZaMV), lane 3 was loaded with CMV-infected *Nicotiana benthamiana*, lane 4 was loaded with CymMV-infected *Phalaenopsis* spp., lane 5 was loaded with HCRSV-infected kenaf (*Hibiscus cannabinus*), lane 6 was loaded with TMV-infected *Nicotiana benthamiana*, and lane 7 was loaded with ZaMV-infected *Philodendron selloum*.

Accordingly, these primers only generated a specific 1.0-kb RT-PCR product with ZaMV (potyvirus), they did not amplify any specific product with CMV (cucumovirus), CymMV (potexvirus), HCRSV (tombusvirus) and TMV (tobamovirus) (FIGS. 2B and 2C).

EXAMPLE 2

Virus Detection and cDNA Cloning

Figure 3A:
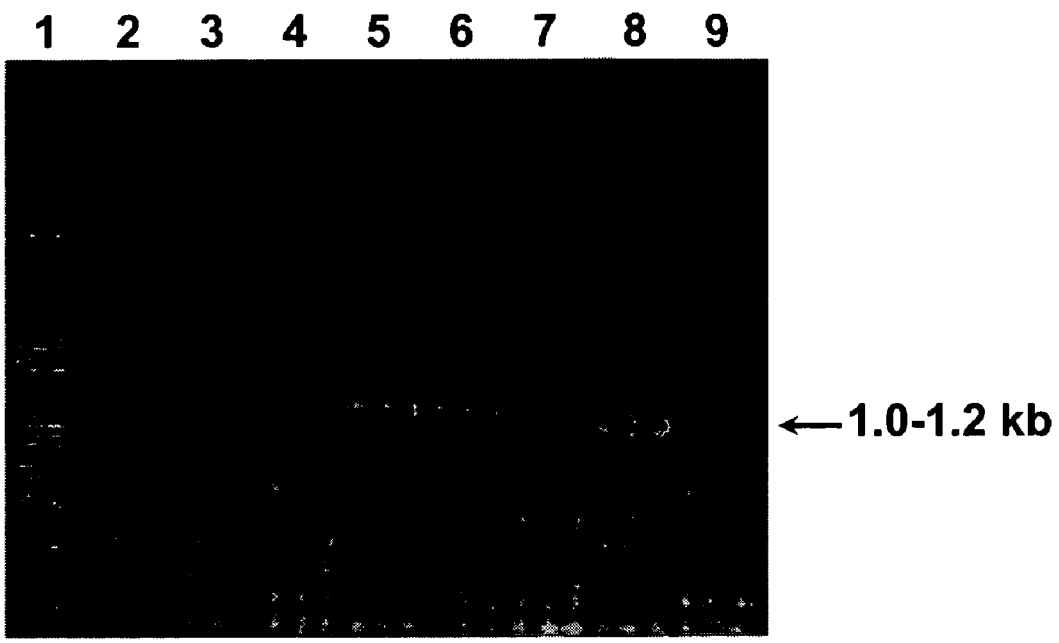
FIG. 3A is an agarose gel image showing RT-PCR product amplified from virus-infected plant total RNA by degenerate primers PCRR1 and PNIbF0.

To confirm further the application spectrum of these degenerate primers, eight different potyviruses were detected separately in inoculated propagation hosts by RT-PCR using PCPR1 as the RT primer and subsequently using PCPR1/PNIbF0 as PCR primers. The expected band on the agarose gel after RT-PCR amplification was about 1.0-1.2 kb. DsMV, ZaMMV, TuMV and PRSV had RT-PCR products about 1.2 kb amplified by PCPR1/PNIbF0 primers (FIG. 3A), whereas ZaMV, ZYMV, PVA and PVY had RT-PCR products of about 1.0 kb amplified by PCPR1/PNIbF0 primers (FIG. 3A).

Figure 3B:
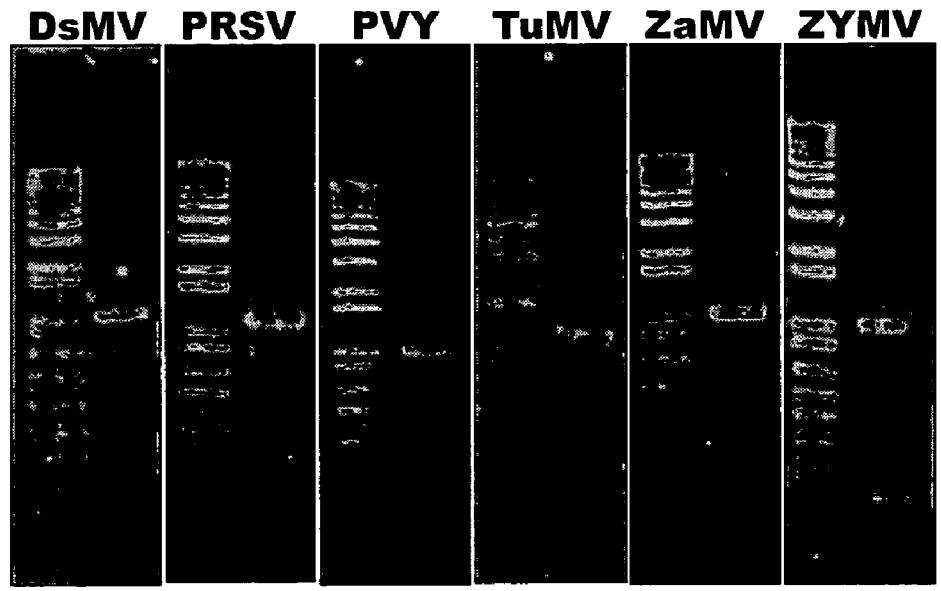
FIG. 3B is an agarose gel image showing RT-PCR product amplified from virus-infected plant total RNA by degenerate primers PCRR1 and PNIbF1 or PCPR1 and PNIbF5.

Alternatively, six different potyviruses were detected separately in inoculated propagation hosts by RT-PCR using PCPR1 as the RT primer and subsequently using PCPR1/PNIbF1 or PCPR1/PNIbF5 as PCR primers. The expected band on the agarose gel after RT-PCR amplification was about 1.0-1.2 kb. PRSV and TuMV had RT-PCR products about 1.2 kb amplified by PCPR1/PNIbF1 primers (FIG. 3B). DsMV, PVY, ZaMV and ZYMV had RT-PCR products about 1.0 kb amplified by PCPR1/PNIbF5 primers (FIG. 3B).

In addition, all RT-PCR products were derived from the expected viruses, as confirmed by sequence analysis after cDNA cloning. Accordingly, these potyvirus degenerate primers had the potential to detect the members of the genus *Potyvirus*.

EXAMPLE 3

Specificity of the Species-Specific cDNA Probes

Two types of cDNA probes were prepared for each potyvirus by PCR amplification. The "potyvirus"-P2 probes started from "potyvirus"-F1 primer and ended at PCPR1 primer. The "potyvirus"-P3 probes started from "potyvirus"-F1 primer and ended at "potyvirus"-R1 primer (Table 1). The specificity of the species-specific cDNA probes was evaluated by dot blot hybridization. Next, 3 ng of unlabeled P2 and P3 probes were immobilized onto a nylon membrane and each probe had a duplicate. And 10 ng of the DIG-labeled PCR fragment of each virus selective clone amplified with primers PCPR1 and PNIbF0 was used to hybridize with the nylon membrane immobilized with the probes. Accordingly, the P2 and P3 probes hybridized with target virus without non-specific hybridization to non-target virus (not shown).

Moreover, the PCR fragments of each virus clone amplified by PCPR1 and PNIbF1 were applied to a nylon membrane. The DIG-labeled species-specific probes were used for hybridization. Accordingly, the cross-hybridization was observed in PCR fragments with the P2 probes of PRSV, PVY, TuMV and ZYMV.

EXAMPLE 4

Virus Identification by Reverse Dot Blot Hybridization Using Species-Specific cDNA Probes The species-specific cDNA probes and revere dot blot hybridization were adopted to identify different potyviruses from infected tissues in a single test. The species-specific cDNA probes "potyvirus"-P2 and "potyvirus"-P3 corresponding to DsMV, ZaMV, ZaMMV, TuMV, PRSV, ZYMV, PVA and PVY were prepared according to the method above. As shown in FIG. 4A, 3 ng of unlabeled P2 and P3 probes were immobilized onto a nylon membrane and each probe had a triplicate. The reverse dot blot hybridizations were performed by hybridizing 20 ng of the DIG-labeled test samples onto the nylon membrane immobilized with the probes. The test samples were prepared by amplifying the infected plant total RNA with potyvirus degenerate primers in RT-PCR. The immobilized probes recognized correctly all of the viruses tested, including DsMV, ZaMV, ZaMMV, TuMV, PRSV, ZYMV, PVA and PVY, when the fragments of the test sample were amplified with PCPR1/PNIbF0 primers (FIG. 4B). And no cross-hybridization was not observed in these reverse dot blot hybridizations.

Next, these species-specific cDNA probes and revere dot blot hybridization were tested for identifying different potyviruses from infected tissues in a single test. At first, 5 ng of unlabeled P2 and P3 probes were immobilized onto a nylon membrane and each probe had a duplicate (FIG. 6A). The reverse dot blot hybridizations were performed by hybridizing with 6 ng of the DIG-labeled test samples which were RT-PCR amplified from the infected plant total RNA by potyvirus degenerate primers. The immobilized probes recognized correctly all of the viruses tested, including DsMV, PRSV, PVY, TuMV, ZaMV and ZYMV, irrespective of whether the fragments of the test sample were amplified with PCPR1/PNIbF1 or PCPR1/PNIbF5 primers (FIG. 6B). And no cross-hybridization was observed in these reverse dot blot hybridizations.

EXAMPLE 5

Figures 5A, 5B:
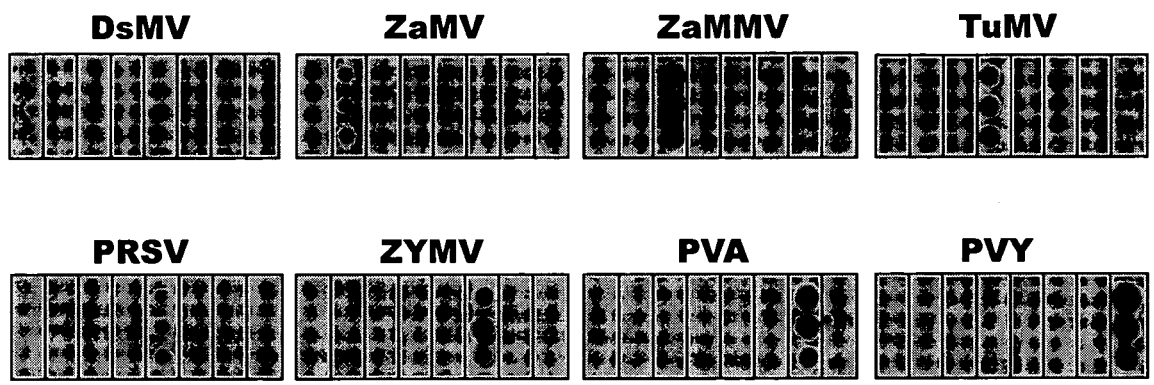
FIG. 5A is a schematic diagram illustrating locations of species-specific oligonucleotide probes on a dot blot image according to one embodiment of the invention.
FIG. 5B is a dot blot image showing the targets hybridized with the species-species oligonucleotide probes arranged according to FIG. 5A.

Virus Identification by Reverse Dot Blot Hybridization Using Species-Specific Oligonucleotide Probes Next, these species-specific oligonucleotide probes and revere dot blot hybridization were tested for identifying different potyviruses from infected tissues in a single test. A 50 mer probe in a variable region between the 3' end of the NIb gene and the 5' end of the CP gene was designed according to sequence alignment. Then, the 50 mer oligonucleotide probe was then prepared by the manufacturer according to the design. As shown in FIG. 5A, 30 pmol of unlabelled oligonucleotide probes were immobilized on the nylon membrane, wherein each probe had a triplicate. A test sample was prepared by amplifying via RT-PCR the total RNA of the plant infected with DsMV, ZaMV, ZaMMV, TuMV, PRSV, ZYMV, PVA and PVY. The test sample (200 ng) labeled with DIG was subjected to reverse dot blot hybridization on the nylon membrane. The immobilized probes recognized correctly all of the viruses tested, including DsMV, ZaMV, ZaMMV, TuMV, PRSV, ZYMV, PVA and PVY, when the fragments of the test sample were amplified with PCPR1/PNIbF0 primers (FIG. 5B).

EXAMPLE 6

Virus Identification of the Plant Mix-Infected by Potyviruses

The plant simultaneously infected with a combination of ZaMV, ZaMMV and TuMV was screened by ELISA in the experiment. The total RNA of the plant was extracted and amplified with primers PCPR1/PNIbF0 before labeling with DIG to serve as a test sample. The P2 and P3 cDNA probes corresponding to eight potyviruses were prepared according to the example 3 and immobilized on a nylon membrane in an arrangement shown in FIG. 4A. Next, the reverse dot blot hybridization was performed according to the example 4. As shown in FIG. 7A, the test sample prepared from the mix-infected plant can hybridize with the P2 and P3 cDNA probes corresponding to ZaMV, ZaMMV and TuMV. Also, the oligonucleotide probes corresponding to eight potyviruses were prepared according to the example 5 and immobilized on a nylon membrane in an arrangement shown in FIG. 5A. Next, the reverse dot blot hybridization was performed according to the example 5. As shown in FIG. 7B, the test sample prepared from the mix-infected plant can also hybridize with the oligonucleotide probes corresponding to ZaMV, ZaMMV and TuMV, without having non-specific reaction with other probes.

In addition, to further identify different potyviruses in mixed infection, total RNAs extracted separately from PRSV-infected and ZYMV-infected plants were mixed to mimic mixed infection sample before reverse dot blot hybridization was performed. The test sample fragments were amplified separately with PCPR1/PNIbF1 and PCPR1/PNIbF5 primers and subsequently hybridized with the blots as previously described. The result demonstrated that both kinds of the test samples prepared from the mixed total RNAs of PRSV-infected and ZYMV-infected plants could react with the P2 and P3 probes of both viruses (FIG. 8A). A plant infected simultaneously by ZaMV and TuMV was used as the test sample amplified by PCPR1/PNIbF1 and then hybridized with the blots as before. The result indicated that the test sample from the mixed infection plant could hybridize with both ZaMV and TuMV cDNA probes although the signals of the P3 probes were weaker than those of the P2 probes (FIG. 8B).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

---

We claim:

1. A method for identifying a target virus in an infected subject comprising
   (i) obtaining a total nucleic acid preparation of the infected subject;
   (ii) preparing a test sample by amplifying the total nucleic acid preparation of the infected subject with a first pair of primers comprising a forward degenerate primer comprising a nucleotide sequence encoding a first highly conserved amino acid sequence of the target virus, and a reverse degenerate primer, the complete complementary sequence of the reverse degenerate primer comprising a nucleotide sequence encoding a second highly conserved amino acid sequence of the target virus;
   (iii) contacting the test sample with a species-specific probe, the species-specific probe being prepared by amplifying the target virus gene sequence with a second pair of primers comprising:
   TuMV-F1 of SEQ ID NO: 7, and TuMV-R1 of SEQ ID NO: 15; and
   (iv) detecting a hybridization between the species-specific probe and the test sample, wherein the hybridization indicates the target virus is identified in the infected subject.

2. The method according to claim 1, wherein contacting the test sample with the species-specific probe of the target virus comprises reverse dot blot hybridization.

3. The method according to claim 1, wherein the test sample is prepared by reverse transcription polymerase chain reaction (RT-PCR).

4. The method according to claim 1, wherein the species-specific probe is immobilized with a nylon membrane.

5. The method according to claim 1, wherein the target virus species is a potyvirus species.

6. An isolated species-specific primer pair for detecting potyviruses, comprising:
   TuMV-F1 of SEQ ID NO: 7, and TuMV-R1 of SEQ ID NO: 15.

7. An isolated species-specific oligonucleotide probe for detecting potyviruses comprising TuMV-O1 of SEQ ID NO: 23.

8. The method according to claim 1, wherein the first pair of primers comprises
   a forward degenerate primer comprising
   PNIbF0:    5'AGAGGNAAYAAYAGYGGNCARCC3' (SEQ ID NO: 1),
   and a reverse degenerate primer comprising
   PCPR1:    5'GGGGAGGTGCCGTTCTCDATRCACCA3' (SEQ ID NO: 2),
   wherein R is adenine (A) or guanine (G), Y is C or thymine (T), B is C, G or T, D is A, G or T, and N is A, C, G or T.

9. The method according to claim 5, wherein the potyvirus species is one or more selected from the group consisting of Dasheen mosaic virus (DsMV), Papaya ringspot virus (PRSV), Potato virus A (PVA), Potato virus Y (PVY), Turnip mosaic virus (TuMV), Zantedeschia mosaic virus (ZaMV), Zantedeschia mild mosaic virus (ZaMMV) and Zucchini yellow mosaic virus (ZYMV).

10. A method for identifying a target virus in an infected subject comprising
    (i) obtaining a total nucleic acid preparation of the infected subject;
    (ii) preparing a test sample by amplifying the total nucleic acid preparation of the infected subject with a pair of primers comprising a forward degenerate primer comprising a nucleotide sequence encoding a first highly conserved amino acid sequence of the target virus, and a reverse degenerate primer, the complete complementary sequence of the reverse degenerate primer comprising a nucleotide sequence encoding a second highly conserved amino acid sequence of the target virus;
    (iii) contacting the test sample with a species-specific oligonucleotide probe; wherein the species-specific oligonucleotide probe comprises TuMV-O1 of SEQ ID NO: 23; and
    (iv) detecting a hybridization between the species-specific probe and the test sample, wherein the hybridization indicates the target virus is identified in the infected subject.

11. The method according to claim 10, wherein the target viruses are potyviruses.

12. The method according to claim 10, wherein the pair of primers comprise
    a forward degenerate primer comprising
    PNIbF0:    5'AGAGGNAAYAAYAGYGGNCARCC3' (SEQ ID NO: 1),
    and a reverse degenerate primer comprising
    PCPR1:    5'GGGGAGGTGCCGTTCTCDATRCACCA3' (SEQ ID NO: 2),
    wherein R is adenine (A) or guanine (G), Y is C or thymine (T), B is C, G or T, D is A, G or T, and N is A, C, G or T.

* * * * *

SEQUENCE LISTING

```
<160> NUMBER OF SEQ ID NOS: 28

<210> SEQ ID NO 1
<211> LENGTH: 23
<212> TYPE: DNA
<213> ORGANISM: Artificial Sequence
<220> FEATURE:
<221> NAME/KEY: misc_feature
<222> LOCATION: (6)..(21)
<223> OTHER INFORMATION: primer sequence, where
      r = a, g; y = c, t; n = a, c, g, t

<400> SEQUENCE: 1
agaggnaaya ayagyggnca rcc                                          23

<210> SEQ ID NO 2
<211> LENGTH: 26
```

```
<212> TYPE: DNA
<213> ORGANISM: Artificial Sequence
<220> FEATURE:
<221> NAME/KEY: misc_feature
<222> LOCATION: (18)..(21)
<223> OTHER INFORMATION: primer sequence, where r = a, g; d = a, g, t

<400> SEQUENCE: 2
ggggaggtgc cgttctcdat rcacca                                          26

<210> SEQ ID NO 3
<211> LENGTH: 24
<212> TYPE: DNA
<213> ORGANISM: Artificial Sequence
<220> FEATURE:
<223> OTHER INFORMATION: primer sequence

<400> SEQUENCE: 3
aaatgtgaag gagtgcgaac ttca                                            24

<210> SEQ ID NO 4
<211> LENGTH: 20
<212> TYPE: DNA
<213> ORGANISM: Artificial Sequence
<220> FEATURE:
<223> OTHER INFORMATION: primer sequence

<400> SEQUENCE: 4
agtaagcgtg ggtcaatgga                                                 20

<210> SEQ ID NO 5
<211> LENGTH: 25
<212> TYPE: DNA
<213> ORGANISM: Artificial Sequence
<220> FEATURE:
<223> OTHER INFORMATION: primer sequence

<400> SEQUENCE: 5
tctatccagt ttgatgaaca aatgg                                           25

<210> SEQ ID NO 6
<211> LENGTH: 21
<212> TYPE: DNA
<213> ORGANISM: Artificial Sequence
<220> FEATURE:
<223> OTHER INFORMATION: primer sequence

<400> SEQUENCE: 6
tggatgagga agagctgaga g                                               21

<210> SEQ ID NO 7
<211> LENGTH: 22
<212> TYPE: DNA
<213> ORGANISM: Artificial Sequence
<220> FEATURE:
<223> OTHER INFORMATION: primer sequence

<400> SEQUENCE: 7
ccagctcaag aagatcttac tc                                              22

<210> SEQ ID NO 8
<211> LENGTH: 22
<212> TYPE: DNA
<213> ORGANISM: Artificial Sequence
<220> FEATURE:
<223> OTHER INFORMATION: primer sequence
```

```
<400> SEQUENCE: 8
tcgtgatgct aatgaggagg ag                                        22

<210> SEQ ID NO 9
<211> LENGTH: 23
<212> TYPE: DNA
<213> ORGANISM: Artificial Sequence
<220> FEATURE:
<223> OTHER INFORMATION: primer sequence

<400> SEQUENCE: 9
ctcacatatg atgaggatga ggg                                       23

<210> SEQ ID NO 10
<211> LENGTH: 21
<212> TYPE: DNA
<213> ORGANISM: Artificial Sequence
<220> FEATURE:
<223> OTHER INFORMATION: primer sequence

<400> SEQUENCE: 10
actggcacga tacctacaag c                                         21

<210> SEQ ID NO 11
<211> LENGTH: 23
<212> TYPE: DNA
<213> ORGANISM: Artificial Sequence
<220> FEATURE:
<223> OTHER INFORMATION: primer sequence

<400> SEQUENCE: 11
aacttccttg cctttctcac ttg                                       23

<210> SEQ ID NO 12
<211> LENGTH: 23
<212> TYPE: DNA
<213> ORGANISM: Artificial Sequence
<220> FEATURE:
<223> OTHER INFORMATION: primer sequence

<400> SEQUENCE: 12
ctctccagtt tttgtgctag ttg                                       23

<210> SEQ ID NO 13
<211> LENGTH: 22
<212> TYPE: DNA
<213> ORGANISM: Artificial Sequence
<220> FEATURE:
<223> OTHER INFORMATION: primer sequence

<400> SEQUENCE: 13
ttcacggcta cagctttgct ac                                        22

<210> SEQ ID NO 14
<211> LENGTH: 22
<212> TYPE: DNA
<213> ORGANISM: Artificial Sequence
<220> FEATURE:
<223> OTHER INFORMATION: primer sequence

<400> SEQUENCE: 14
tgttcgggtt tgactggatg ct                                        22

<210> SEQ ID NO 15
<211> LENGTH: 20
```

```
<212> TYPE: DNA
<213> ORGANISM: Artificial Sequence
<220> FEATURE:
<223> OTHER INFORMATION: primer sequence

<400> SEQUENCE: 15
tcgcgttcac cctcttcttg                                              20

<210> SEQ ID NO 16
<211> LENGTH: 22
<212> TYPE: DNA
<213> ORGANISM: Artificial Sequence
<220> FEATURE:
<223> OTHER INFORMATION: primer sequence

<400> SEQUENCE: 16
gtgtgtttgc acttgtttgt tc                                           22

<210> SEQ ID NO 17
<211> LENGTH: 22
<212> TYPE: DNA
<213> ORGANISM: Artificial Sequence
<220> FEATURE:
<223> OTHER INFORMATION: primer sequence

<400> SEQUENCE: 17
cagatctctt tggccttggg tt                                           22

<210> SEQ ID NO 18
<211> LENGTH: 22
<212> TYPE: DNA
<213> ORGANISM: Artificial Sequence
<220> FEATURE:
<223> OTHER INFORMATION: primer sequence

<400> SEQUENCE: 18
cttggcagct actactgttt tc                                           22

<210> SEQ ID NO 19
<211> LENGTH: 50
<212> TYPE: DNA
<213> ORGANISM: Artificial Sequence
<220> FEATURE:
<223> OTHER INFORMATION: oligonucleotide probe

<400> SEQUENCE: 19
gcgatatttg gatgctttca actttgagtt attctgtgag catgatgaag             50

<210> SEQ ID NO 20
<211> LENGTH: 50
<212> TYPE: DNA
<213> ORGANISM: Artificial Sequence
<220> FEATURE:
<223> OTHER INFORMATION: oligonucleotide probe

<400> SEQUENCE: 20
gtagataaat attttgagcg agaaagggga gattcacctg agctactggt             50

<210> SEQ ID NO 21
<211> LENGTH: 50
<212> TYPE: DNA
<213> ORGANISM: Artificial Sequence
<220> FEATURE:
<223> OTHER INFORMATION: oligonucleotide probe

<400> SEQUENCE: 21
```
tctatccagt ttgatgaaca aatggatgaa gaagatgaca tggtgtattt    50

<210> SEQ ID NO 22
<211> LENGTH: 50
<212> TYPE: DNA
<213> ORGANISM: Artificial Sequence
<220> FEATURE:
<223> OTHER INFORMATION: oligonucleotide probe

<400> SEQUENCE: 22
agagccttca ctgaaatgat ggtcgcatta gacgatgagt ttgaatttga    50

<210> SEQ ID NO 23
<211> LENGTH: 50
<212> TYPE: DNA
<213> ORGANISM: Artificial Sequence
<220> FEATURE:
<223> OTHER INFORMATION: oligonucleotide probe

<400> SEQUENCE: 23
gcaatctttg aggattatga agacggtact gagacttgtg tttatcacca    50

<210> SEQ ID NO 24
<211> LENGTH: 50
<212> TYPE: DNA
<213> ORGANISM: Artificial Sequence
<220> FEATURE:
<223> OTHER INFORMATION: oligonucleotide probe

<400> SEQUENCE: 24
ctaaggtatg ccactgaaca gagcattgaa tggccacagg aggaacaagt    50

<210> SEQ ID NO 25
<211> LENGTH: 50
<212> TYPE: DNA
<213> ORGANISM: Artificial Sequence
<220> FEATURE:
<223> OTHER INFORMATION: oligonucleotide probe

<400> SEQUENCE: 25
tgttgaagtc ctcacatatg atgaggatga ggggtgtggc gaggatgtcg    50

<210> SEQ ID NO 26
<211> LENGTH: 50
<212> TYPE: DNA
<213> ORGANISM: Artificial Sequence
<220> FEATURE:
<223> OTHER INFORMATION: oligonucleotide probe

<400> SEQUENCE: 26
cctccatcaa gatatcttct ttgaacaagg agacactgta atgctccaat    50

<210> SEQ ID NO 27
<211> LENGTH: 20
<212> TYPE: DNA
<213> ORGANISM: Artificial Sequence
<220> FEATURE:
<221> NAME/KEY: misc_feature
<222> LOCATION: (3)..(15)
<223> OTHER INFORMATION: primer sequence, where
      b = c, g, t; y = c, t; n = a, c, g, t

<400> SEQUENCE: 27
ggbaayaata gtggncaacc    20

<210> SEQ ID NO 28

```
<211> LENGTH: 25
<212> TYPE: DNA
<213> ORGANISM: Artificial Sequence
<220> FEATURE:
<221> NAME/KEY: misc_feature
<222> LOCATION: (17)..(23)
<223> OTHER INFORMATION: primer sequence, where
      y = c, t; n = a, c, g, t

<400> SEQUENCE: 28
gccagccctc caccgtngtn gayaa                                          25
```